US 9,265,878 B2

(12) United States Patent
McGhie

(10) Patent No.: US 9,265,878 B2
(45) Date of Patent: Feb. 23, 2016

(54) BIOPSY NEEDLE STAND

(75) Inventor: Thomas W. McGhie, Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 1040 days.

(21) Appl. No.: 13/400,191

(22) Filed: Feb. 20, 2012

(65) Prior Publication Data

US 2012/0265098 A1    Oct. 18, 2012

Related U.S. Application Data

(60) Provisional application No. 61/474,789, filed on Apr. 13, 2011.

(51) Int. Cl.
- *A61M 5/00* (2006.01)
- *A61B 17/34* (2006.01)
- *A61B 10/02* (2006.01)

(52) U.S. Cl.
CPC ............ *A61M 5/008* (2013.01); *A61B 17/3403* (2013.01); *A61B 10/0233* (2013.01); *A61B 2017/3407* (2013.01)

(58) Field of Classification Search
CPC ............... A61B 17/3403; A61B 17/06061; A61B 17/06066; A61B 17/06114; A61B 17/06; A61B 10/0233; A61B 10/0241; A61B 10/025; A61B 10/0096; A61B 2010/0258; A61B 2017/3407; A61B 2017/3405; A61B 2017/3409; A61B 2017/3411; A61B 5/150732; A61B 19/0256; A61B 2019/0258; A61B 2019/0259; A61M 5/008; A61M 5/1414; A61M 25/02; B01L 2200/022; B01L 2200/025; B01L 2200/023; B01L 9/00; B01L 9/04; B01L 9/06; B01L 9/065; B01L 9/54; B01L 9/543; B01L 9/547; G01N 2035/00801; G01N 21/253; G01N 2035/0401; G01N 2035/0412; G01N 2035/0439; G01N 35/026; A45C 11/36; B25H 3/00; B25H 3/003; A61J 1/2055

See application file for complete search history.

(56) References Cited

U.S. PATENT DOCUMENTS

| | | | | |
|---|---|---|---|---|
| 4,325,485 A | * | 4/1982 | Pina et al. | 211/66 |
| D333,769 S | * | 3/1993 | Jureckson | D6/682.2 |
| 5,615,782 A | * | 4/1997 | Choe | 211/70.6 |
| 5,687,855 A | * | 11/1997 | Heller | 211/65 |
| D480,246 S | * | 10/2003 | Hood | D6/534 |
| D538,091 S | * | 3/2007 | Roth | D6/534 |
| D545,062 S | * | 6/2007 | Nagoya | D4/113 |
| 2005/0098510 A1 | * | 5/2005 | Lom et al. | 211/13.1 |
| 2010/0033027 A1 | | 2/2010 | Fan et al. | |

FOREIGN PATENT DOCUMENTS

| | | |
|---|---|---|
| EP | 1 929 972 A1 | 6/2008 |
| WO | WO 2008/062474 A2 | 5/2008 |

* cited by examiner

*Primary Examiner* — Jocelin Tanner
(74) *Attorney, Agent, or Firm* — Woodard, Emhardt, Moriarty, McNett & Henry LLP

(57) ABSTRACT

Embodiments of a needle stand are disclosed that include a base, an arching boom, and a tube, wherein the needle stand supports a biopsy needle. The base defines a plane and the base is configured to attach to a patient. The boom is attached to the base and has a length and a convex curvature and defines a plurality of holes along all or a portion of the length. The tube is sized to retain a needle handle of the biopsy needle. Each of the plurality of holes is sized to retain the tube and each of the plurality of holes defines an axis. The plane and each of the axes form a unique point of entry angle for the biopsy needle. In one embodiment, each of the plurality of holes is spaced at an interval along the boom that corresponds to about 10° increment in the angle.

20 Claims, 3 Drawing Sheets

BIOPSY NEEDLE STAND

REFERENCE TO RELATED APPLICATION

This application claims the benefit of U.S. Provisional Patent Application No. 61/474,789, filed Apr. 13, 2011, which is herein incorporated by reference in its entirety.

BACKGROUND

The present disclosure relates generally to a needle stand for a biopsy needle and more particularly to a needle stand that is easily and quickly adjustable to account for the three degrees of freedom for the entry of the biopsy needle in the patient.

Tissue sampling in which soft tissue biopsy needles are used may require situations in which the clinician needs to release the needle after inserting it at least part of the way to targeted tissue, leaving it cantilevered in the patient. For example, there may be a need to use fluoroscopy or other imaging to confirm proper needle placement, or to move the patient to a different treatment or imaging room. As another example, the clinician may need to rest or reorient himself or herself to appropriately support the needle.

Often a needle stand is used to support a partially- or fully-inserted biopsy needle cantilevered in the patient. Typically, a needle stand can also be used to guide and stabilize the needle at a chosen angle and location while the needle is inserted through the skin of a patient. The support and maintenance of position provided by a needle stand frees the clinician to perform other tasks that may also be required during the medical procedure.

One type of needle stand currently used includes a clip for holding a needle and a guide arrangement for supporting the clip and directing the needle at a desired angle relative to the patient's body. The clip is attached to a rail portion of the guide arrangement, and the position of the clip is adjustable laterally along the rail portion as the clinician may need for the particular patient. The clip includes a releasable connection such that the needle can be disengaged from the guide arrangement by a lateral movement of the clip and/or guide arrangement relative to the longitudinal axis of the needle. Moreover, the needle handle is not directly supported by the clip. Instead, a portion of the thin needle structure is supported by the clip and rail portion. As can be appreciated, the thin needle is a relatively weak portion, that can be broken or otherwise damaged while retained in the clip. Differently-sized clips are required for each stand, so as to match the gauge of the needle sleeve and needle cannula that are used, because the needle cannula may jiggle or shake in the clip if the clip does not hold the needle cannula firmly. The needle stand also typically includes a base for support itself when placed on a body surface. The guide arrangement is hingedly connected to the base to allow for adjustment of the desired angle of the needle. Therefore, adjustment of the orientation of the needle requires adjusting the clip laterally on the rail portion and adjusting the guide arrangement about the hinge on the base. Adjusting all of these components is complicated, requires moving many parts to accomplish the change, and is time consuming for the clinician.

In lieu of a needle stand, a medical practitioner may simply hold the needle in place while image guidance or fluoroscopy is used to locate the biopsy needle within the patient. As such, there is a risk that the medical practitioner will be exposed to X-rays or other radiation during the image guidance. Alternatively, the medical practitioner may tape the biopsy needle against the skin of the patient. However, tape can be ineffective when used on a biopsy needle in maintaining the desired position and depth of the needle.

Thus, there is a need for improvement in this field.

SUMMARY

This Summary is provided merely to introduce certain concepts and not to identify any key or essential features of the claimed subject matter.

In certain of its aspects, the present disclosure features a needle stand that supports a biopsy needle during a medical procedure. The needle stand includes a tube and a stand that consists of an arching boom attached to a base. The tube is sized to retain and hold a needle handle of the biopsy needle. The base has a plurality of legs configured to support the arching boom that is attached to the base. The arching boom has a length with convex curvature and also defines a plurality of holes. Each of the plurality of holes is sized to retain the tube. As such, the needle handle is inserted in the tube, and the combined needle and tube is inserted in one of the plurality of holes. In one form, the plurality of legs includes two legs, and the legs are separated from each other by or include between them an angle of about 90°. In another form, the plurality of legs includes three legs that are in the same plane. In another embodiment, each of the plurality of legs has a top surface opposite a bottom surface, and the bottom surface includes an adhesive suitable to attach the base to a patient. Optionally, the length of the arching boom is about 7.0 cm.

In other of its aspects, the present disclosure features a stand that includes a base and an arching boom. The base defines a plane, and the base is configured to attach to or be placed upon a patient. The boom is attached to the base. The boom has a length that has a convex curvature and defines a plurality of holes along all of or a portion of the length. Each of the plurality of holes is sized to retain the biopsy needle, and each of the plurality of holes defines an axis. The plane and each of the axes form a respective point of entry angle for the biopsy needle. In one embodiment, each of the plurality of holes is spaced at an interval along the boom that corresponds to about a 10° increment in the point of entry angle for the biopsy needle. In another embodiment, the stand includes a tube sized to retain a needle handle of the biopsy needle, and each of the plurality of holes is sized to retain the tube. Further, in this embodiment, the tube and the needle handle form an interference fit connection. In one form, the boom includes a centerline along the length, and the plurality of holes are positioned along the centerline. Further, in this form, the centerline divides the boom into a first side opposite a second side. The boom has a proximal boom portion opposite a distal boom portion wherein the distal boom portion defines a slot at the centerline and a pair of key holes. A key is configured to slide in the pair of key holes and selectively squeeze the first and second sides together to secure the tube in one of the plurality of holes. In an alternate form, the plurality of holes are positioned along a side edge of the boom and the plurality of holes are configured to form a snap-fit connection with the tube.

In yet other of its aspects, the present disclosure features a method of supporting a biopsy needle during a medical procedure. The method includes providing a needle stand, the needle stand including a tube sized to retain a needle handle of the biopsy needle, a base having a plurality of legs, and an arching boom attached to the base so that the base supports the boom. The boom has a length that has a convex curvature and defines a plurality of holes along its length, and each of the plurality of holes is sized to retain the tube. The method includes inserting the needle handle of the biopsy needle into the tube, selecting a point of entry angle for the biopsy needle into a medical patient, and inserting the tube with the biopsy needle into one of the plurality of holes that corresponds to the point of entry angle.

Further forms, objects, features, aspects, benefits, advantages, and embodiments of the present disclosure will become apparent from a detailed description and drawings provided herewith.

DESCRIPTION OF THE SELECTED EMBODIMENTS

Figure 1:
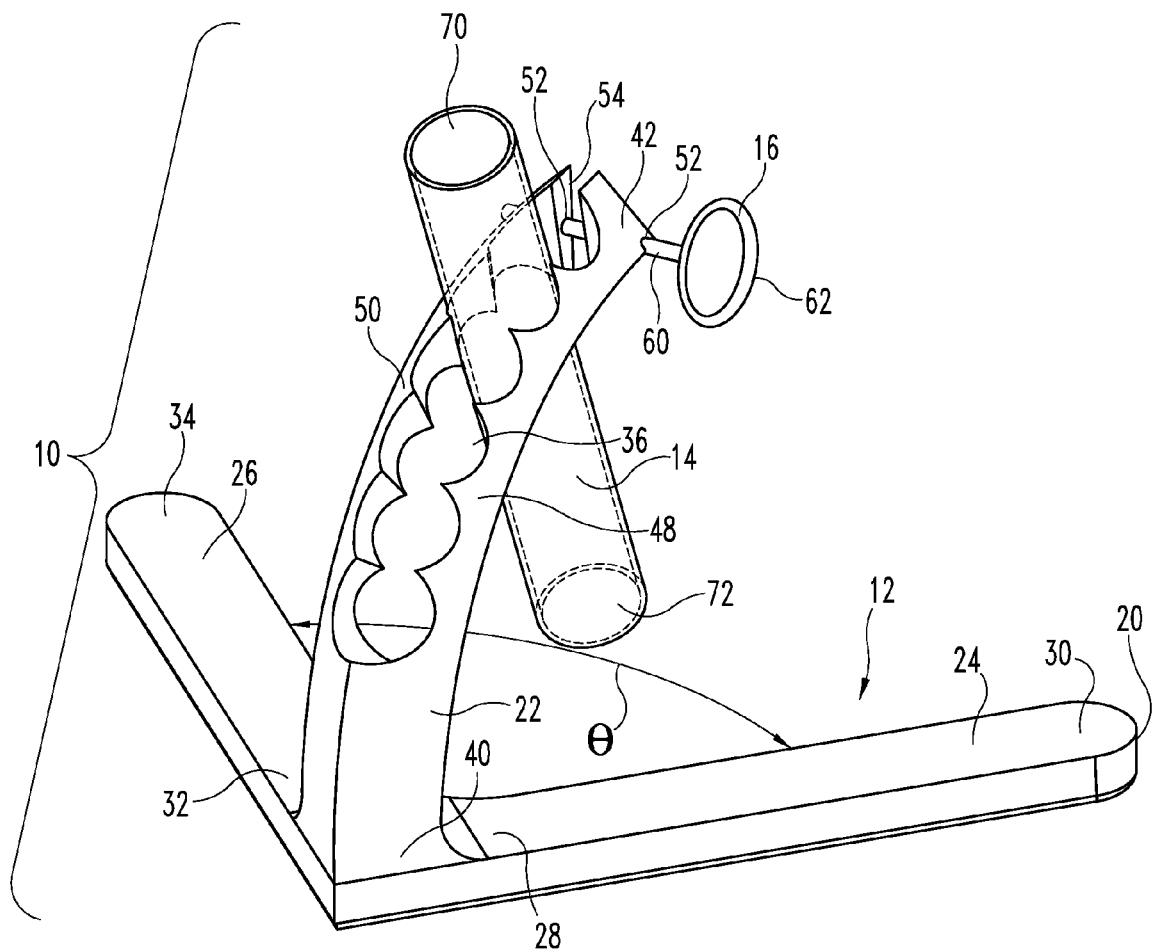
FIG. 1 is a perspective view of one embodiment of a needle stand.

For the purpose of promoting an understanding of the principles of the disclosure, reference will now be made to the embodiments illustrated in the drawings and specific language will be used to describe the same. It will nevertheless be understood that no limitation of the scope of the claims is thereby intended. Any alterations and further modifications in the described embodiments, and any further applications of the principles of the disclosure as described herein are contemplated as would normally occur to one skilled in the art to which the disclosure relates. One embodiment of the disclosure is shown in great detail, although it will be apparent to those skilled in the relevant art that some features that are not relevant to the present disclosure may not be shown for the sake of clarity.

Figure 2:
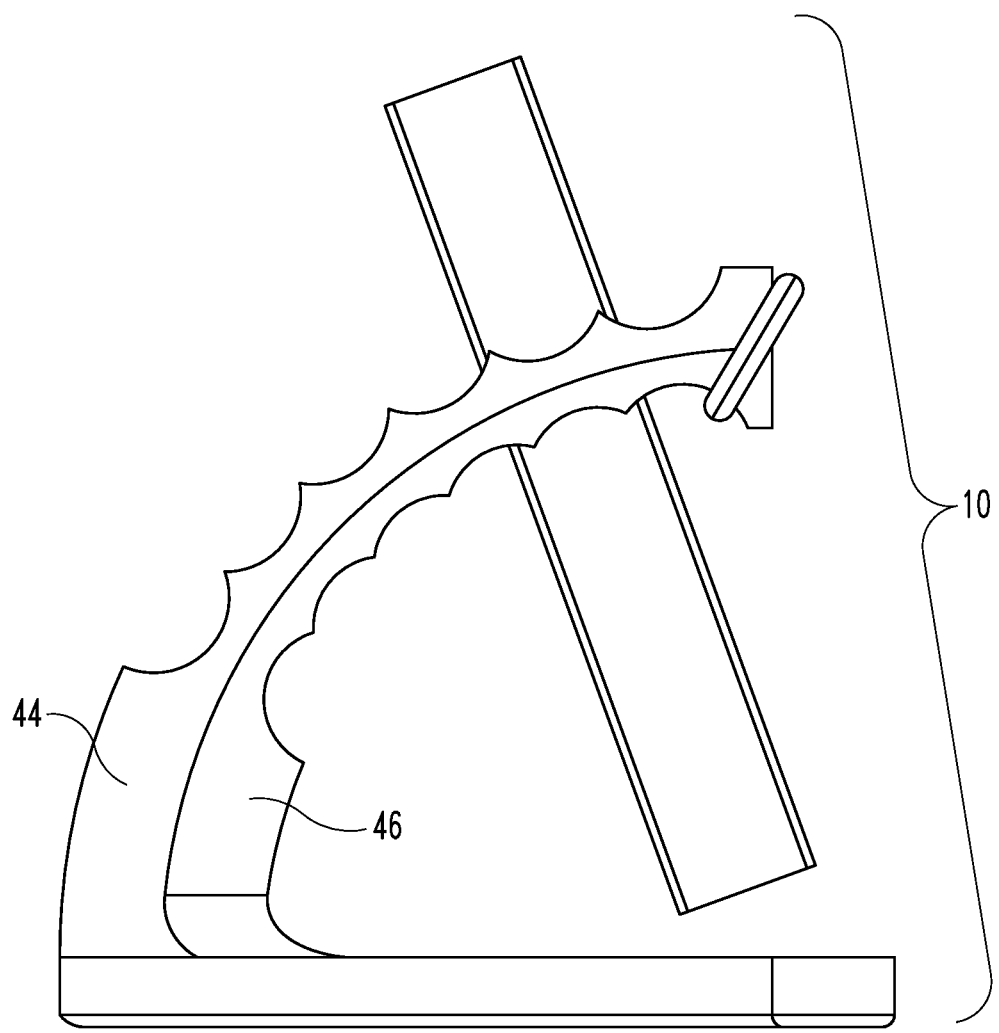
FIG. 2 is a side view of the FIG. 1 embodiment.

Referring generally to FIGS. 1 and 2, one embodiment of a needle stand 10 is illustrated. Needle stand 10 is provided with fewer accessories than other needle stands, is easy to operate, and accounts for the adjustment of all three degrees of freedom for the entry of a biopsy needle into a patient. These three degrees of freedom for the entry of a needle into a patient may be defined as the elevation angle, azimuth angle, and distance. Once the penetration point or point of entry of the biopsy needle into a patient is chosen, the needle stand 10 enables the physician or other clinician to choose one hole on the needle stand 10 to support the biopsy needle that corresponds to the desired angle and point of entry. A clinician can quickly and as frequently as may be necessary adjust the position of the biopsy needle in the needle stand 10. Beneficially, the needle stand 10 is compatible with many needle gauges, so long as the handle interface for each of the needle gauges is the same. For example, needles ranging from 10 gauge to 20 gauge can be used with a single needle stand 10 without any modification if all of these needles use the same needle protector.

Needle stand 10 includes a frame 12, a tube 14, and in some embodiments, a key 16. Frame 12 includes a base 20 connected to an arching boom 22. The base 20 includes a first arm 24 and a second arm 26, indicated as generally elongated member in the illustrated embodiment, wherein the first arm 24 is positioned in the same plane as the second arm 26. In other embodiments, the base 20 includes three or more arms similar to first arm 24 and second arm 26, which may be generally arranged to lie in a single plane. The illustrated embodiment shows the first arm 24 to be approximately the same length as the second arm 26, and in a particular example the first arm 24 and the second arm 26 each have a length of approximately 7.0 centimeters. In other embodiments, the first arm 24 is a different length than the second arm 26.

First arm 24 is fixed to or unitary with and rotationally offset from the second arm 26 by an angle Θ in the illustrated embodiment. The angle Θ shown in FIG. 1 is approximately 90° to provide substantial stability with limited space requirements for its use, although the angle Θ may be different in other embodiments. The first arm 24 includes a proximal arm portion 28 at or adjacent to boom 22, which is opposite a free distal arm portion 30. Similarly to the first arm 24, the second arm 26 includes a proximal arm portion 32 at or adjacent boom 22 and opposite a free distal arm portion 34. In the illustrated embodiment, both arm portions 28 and 32 are substantially rectangular in shape, and both the distal arm portions 30 and 34 are likewise configured out to ends that are generally semi-circular in shape. In other embodiments, the ends of distal arm portions 30 and 34 may be shaped differently, e.g. rectangularly, triangularly, or polygonally. The first and second arms 24 and 26 can be any desired shape, such as plate-like. However, first and second arms 24 and 26 should not include sharp edges or points that may cut a patient's skin.

In one embodiment, the flexibility of first arm 24 and second arm 26 is such that the first and second arms 24 and 26 are able to conform to the skin surface of the patient in the area where the needle is or is to be inserted. For example, when the first arm 24 and second arm 26 are to be positioned on a patient's arm, then the first and second arms 24 and 26 may be very flexible so as to bend along or around the patient's arm. However, when the first and second arms 24 and 26 are intended for positioning on a patient's abdomen, then the first and second arms 24 and 26 may be less flexible and more rigid because the abdomen is typically flatter than an arm. In another embodiment, first and second arms 24 and 26 may be rigid such that the first and second arms 24 and 26 do not conform to the skin surface of the patient in the designated area where the needle will be inserted. In yet another embodiment, first arm 24 may be flexible and second arm 26 may be rigid or vice versa. It is beneficial that the first and second arms 24 and 26 conform to the body part at the incision point because the first and second arms 24 and 26 are typically affixed to the patient's body to secure the needle stand 10. In one embodiment, an adhesive is applied to the bottom surface of the first arm 24 and the second arm 26 to adhere the first and second arms 24 and 26 to the patient. In another embodiment, adhesive tape is applied onto the patient's body and over the first and second arm 24 and 26 to secure the needle stand 10 with respect to the patient.

Boom 22 is positioned between the proximate arm portions 28 and 32, and includes a proximate boom portion 40 opposite a distal boom portion 42. In the illustrated embodiment, boom 22 arches upwardly in a convex manner from the proximate boom portion 40 to the distal boom portion 42, i.e. a generally convex surface or portion points generally away from base 20 and a corresponding concave surface or portion points generally toward base 20. The curvature of boom 22 results in a center of mass for boom 22 located between and above arms 24 and 26. In one form, the arching boom 22 has a length of approximately 7.0 centimeters, although the boom 22 can be longer or shorter in other embodiments.

Boom 22 defines a plurality of holes 36 from the distal boom portion 42 towards the proximate boom portion 40 and positioned along the centerline of boom 22. The diameter of each of the plurality of holes 36 is sized to receive the tube 14, and tube 14 may be accommodated in respective holes 36 in one or more of an interference, friction, loose or adjustable fit. Correspondingly, the inner diameter of tube 14 is sized to receive the needle handle portion of a biopsy needle. For example, a typical needle handle portion has a diameter of about 3.8 mm. In such a case, tube 14 has an internal diameter of about 3.8 mm or less for a close or interference fit with the needle handle portion. Each of the plurality of holes 36 would also have a diameter of larger than about 3.8 mm by at least the thickness of the wall of tube 14 to receive tube 14 therein. In the illustrated embodiment, six holes 36 are provided in boom 22, and each is of the same diameter and overlaps with its adjacent hole(s) 36. Other embodiments may have more or less than six holes 36, or holes that do not overlap or are of different sizes, particularly if boom 22 is significantly larger, smaller or otherwise differently configured than the illustrated embodiment. As can be appreciated, a greater number of holes 36 aids the physician to more precisely choose the desired angle for the biopsy needle to form an incision. One example includes spacing each of the holes 36 along the boom 22 at an interval that corresponds to about 10° increment for the point of entry for a biopsy needle. Other embodiments can have different intervals for spacing each of the holes 36 to correspond to larger or smaller angle increments. This increment is seen in the elevation angle or the angle formed by the plane that includes the first and second arms 24 and 26 and the centerline of the biopsy needle cannula. Beneficially, the curvature of boom 22 and the plurality of holes 36 allows or enables the physician to place tube 14 at different angles with respect to the skin surface of the patient along the length of the boom 22. Comparatively, if boom 22 were straight, then the physician would only be able to place tube 14 at one angle relative to the patient, no matter which one of the plurality of holes 36 is used for tube 14.

In the illustrated embodiment, the cross-sectional shape of the arching boom 22 forms a diamond; however, in other embodiments, the cross-sectional shape may be different. For example, the cross-sectional shape of arching boom 22 may be rectangular, circular, square, oval, polygonal, or another geometric shape. In the illustrated form, the cross-sectional shape of the arching boom 22 is tapered from the proximate boom portion 40 to the distal boom portion 42. In other forms, the cross-sectional shape of the arching boom 22 is constant.

Although the length of boom 22 can be longer or shorter than 7.0 cm, the length of boom 22 is long enough to support a biopsy needle. For example, a long biopsy needle of approximately 20 cm would require a longer boom 22 than compared to a shorter biopsy needle of approximately 15 cm. Moreover, the cross-sectional shape and size of boom 22 must be adequate enough to also support a biopsy needle. As can be appreciated, a heavy biopsy needle requires a larger cross-sectional shape and size of boom 22 to support the biopsy needle as compared to a lighter biopsy needle that would require a smaller cross-sectional shape and size.

Turning now to FIG. 2, boom 22 includes a top surface 44 and a bottom surface 46 that span the length of boom 22. Each of the plurality of holes 36 spans between the top surface 44 and the bottom surface 46 and the plurality of holes 36 is positioned along the centerline of boom 22. Additionally, each of the plurality of holes 36 is aimed radially outward from the center of base 20. The intersection of top surface 44 and each of the plurality of holes 36 is shown as respective concave profiles, as is the intersection of bottom surface 46 and each of the plurality of holes 36. Additionally, the plurality of holes 36 along boom 22 divides it into two portions and creates a first side 48 opposite a second side 50. In the illustrated embodiment, boom 22 also includes a corner substantially aligned with the corner formed by arms 24 and 26, and which corner is substantially aligned with the centers of holes 36.

Looking at FIG. 1, the distal boom portion 42 includes a pair of key holes 52. Each of the key holes 52 is positioned on the first and second sides 48 and 50 and the key holes 52 extend through the width of the first and second sides 48 and 50. Key holes 52 are aligned with each other, and each is sized to receive key 16. In this embodiment, each of key holes 52 is threaded as by opposite-handed threads, so that turning key 16 will move sides 48 and 50 toward or away from each other. Another embodiment would have one of key holes 52 threaded and the other rotatably fitted (e.g. journaled) with key 16 to achieve a similar movement of sides 48 and 50. Distal boom portion 42 defines a slot 54 positioned between the first and second sides 48 and 50 at the end of distal boom portion 42 and communicating with at least the distal-most hole 36. In the illustrated embodiment, when key 16 or another locking mechanism is inserted in the pair of key holes 52 and rotated in a first direction, sides 48 and 50 of boom 22 are squeezed together, narrowing slot 54. Beneficially, the movement of the first and second sides 48 and 50 towards one another applies a compressive force to tube 14 to thereby hold the tube 14 in one of the holes 36 in boom 22 and eliminate or reduce potential movement of the tube 14 relative to the arching boom 22. Although one pair of key holes 52 is illustrated, an alternate embodiment includes a plurality of pairs of key holes 52 positioned along the boom 22 wherein one pair of key holes 52 is positioned near each of the holes 36. The plurality of pairs of key holes 52 further insures that the tube 14 is securely held in one of the holes 36.

As mentioned previously, one type of locking mechanism is key 16 that is placed in the pair of key holes 52 to hold or compress first and second sides 48 and 50 together. Key 16 includes a threaded leg 60 in this embodiment sized to pass through the pair of key holes 52. Key 16 also includes a handle 62 attached to the leg 60 wherein the handle 62 is sized to be operable by a user's fingers or hand. In this embodiment, key 16 is a thumb-screw, and so leg 60 includes thread(s) sized and arranged to engage the threads in one or both of key holes 52. In other embodiments, different forms of a locking mechanism can be used to compress first and second sides 48 and 50 together. Some types of locking mechanisms include a clip, a cotter, a pin, a clamp or other fastener that is configured to compress or hold first and second sides 48 and 50 together. As can be appreciated, the locking mechanism is simple to operate; therefore, the physician can quickly and frequently adjust the longitudinal position of tube 14 in one of the holes 36, and/or move tube 14 from one hole 36 to another as may be necessary.

Tube 14 is a hollow circular cylinder in this embodiment configured and sized to receive and retain a needle handle of a biopsy needle (not illustrated) or other type of needle or syringe. Alternatively, tube 14 may be configured and sized to receive a needle hub on a needle sleeve of a needle. Tube 14 is sized to fit in any of the plurality of holes 36, and tube 14 can be removed from or repositioned in boom 22 as desired. Tube 14 includes a distal end 70 opposite a proximal end 72. When the tube 14 is assembled with a needle, the cutting or tissue-sampling portion of the needle will extend from the proximal end 72 of tube 14 while the handle or hub of the needle is retained in the tube 14 and can extend from the distal end 70. Generally, tube 14 has a similar diameter as a needle protective sleeve used for protecting a needle during shipping.

In an alternate embodiment, tube 14 is separable into shorter lengths. This embodiment includes a separating mechanism in tube 14 that enables a clinician to eliminate excess length of tube 14 as a medical procedure is being conducted or prior to conducting the medical procedure. For example, tube 14 can include a plurality of perforations around the perimeter to enable a clinician to cut or snap tube 14 at the perforations to shorten the length of tube 14 as desired. As another example, tube 14 includes a plurality of segments that are detachable from one another to shorten the length of tube 14. As described next, the adjustability of the length of tube 14 is especially beneficial for a needle with a long length. For example, if a long needle were used with needle stand 10, then a longer length of tube 14 is required to support the long needle during the initial bodily access. However, as the long needle is advanced into the body, the length of tube 14 that extends above the boom 22 would need to be reduced. In one form to reduce the length of tube 14 extending above the boom 22, the tube 14 is advanced towards the skin surface of the patient. To do advance tube 14, key 16 is rotated or unscrewed to enable the first and second sides 48 and 50 to open or spread apart from each other. As such, tube 14 can slide freely in the hole 36. However, as the long needle is advanced into the body and the tube 14 is advanced closer to the skin surface, eventually the tube 14 will run into or contact the skin surface of the patient. Therefore, it is desirable for an easy and quick adjustment mechanism in tube 14 that enables the clinician to shorten the length of tube 14. Beneficially, the separating mechanism included in tube 14 as described in this embodiment enables the clinician to separate a portion of the tube 14 to thereby shorten the length of the tube 14. In one form, the clinician can tear, cut, or snap along the plurality of perforations to remove the proximal end 72 from the tube 14. Beneficially, the frame 12 can be sized to accommodate any length of tube 14 and any length of needle.

In one form, base 20 and boom 22 are made of plastic and formed by a plastic injection mold technique to create stand 12 as one piece. In another form, base 20 is formed separately from arching boom 22, and the two pieces are attached or connected together, as for example where base 20 is desired to have substantially greater flexibility than that of boom 22. In most embodiments, boom 22 may be made out of hard plastics or metals and securely joined to base 20 so that there is minimal flexibility of boom 22 and the relative angles of holes 36 with respect to base 20 (e.g. arms 24 and/or 26) are maintained at least substantially constant. In one embodiment, tube 14 is an extruded plastic tube. Beneficially, there is none or one joint between base 20 and boom 22 which simplifies the manufacture of stand 12 and reduces the production cost. Moreover, since base 20 and arching boom 22 do not move separately from one another, operation of stand 10 is easy and simple.

One technique of adjusting the orientation of the needle stand 10 is described next. Prior to beginning bodily access to a patient with a biopsy needle, tube 14 is affixed to the needle handle or hub portion of the biopsy needle. In other embodiments, tube 14 is attached to other medical devices or another type of needle or syringe. Any time the medical practitioner desires to support the biopsy needle, the medical practitioner would bring the stand 12 near the patient and select the appropriate one of the plurality of holes 36 that is to receive tube 14. By selecting the appropriate one of holes 36, the elevation angle of the biopsy needle in the patient is determined or accounted for. Tube 14 is then inserted into the selected one of holes 36. The height of tube 14 relative to boom 22 is adjusted depending on how much of the needle is protruding from the patient. By selecting the appropriate height of tube 14 relative to boom 22, the length of the needle extending from the patient is determined or accounted for.

In the illustrated embodiment, leg 60 of key 16 is inserted in the pair of key holes 52 (if not already present before insertion of tube 14 through a hole 36), and the first and second sides 48 and 50 are compressed together by turning key 16 to hold the tube 14 in the desired position. Additionally, the azimuth angle of the biopsy needle is determined or accounted for by rotating the needle stand 10 relative to the patient prior to adhering or attaching the needle stand 10 to the patient. In one form, a medical adhesive applied to the bottom surface of the first arm 24 and the second arm 26 enables the first and second arms 24 and 26 to be adhered or attached to the patient. Alternatively, adhesive tape is applied to or over the first and second arms 24 and 26 and the patient to secure base 20 or another portion of frame 12 to the patient. The steps described above to position the needle stand 10 determine or account for the elevation angle, azimuth angle, and length of the needle relative to the patient and can be performed in any order as desired by the medical practitioner. For example, the needle stand 10 can be rotated to account for the azimuth angle prior to selecting the appropriate one of holes 36.

Figure 3:
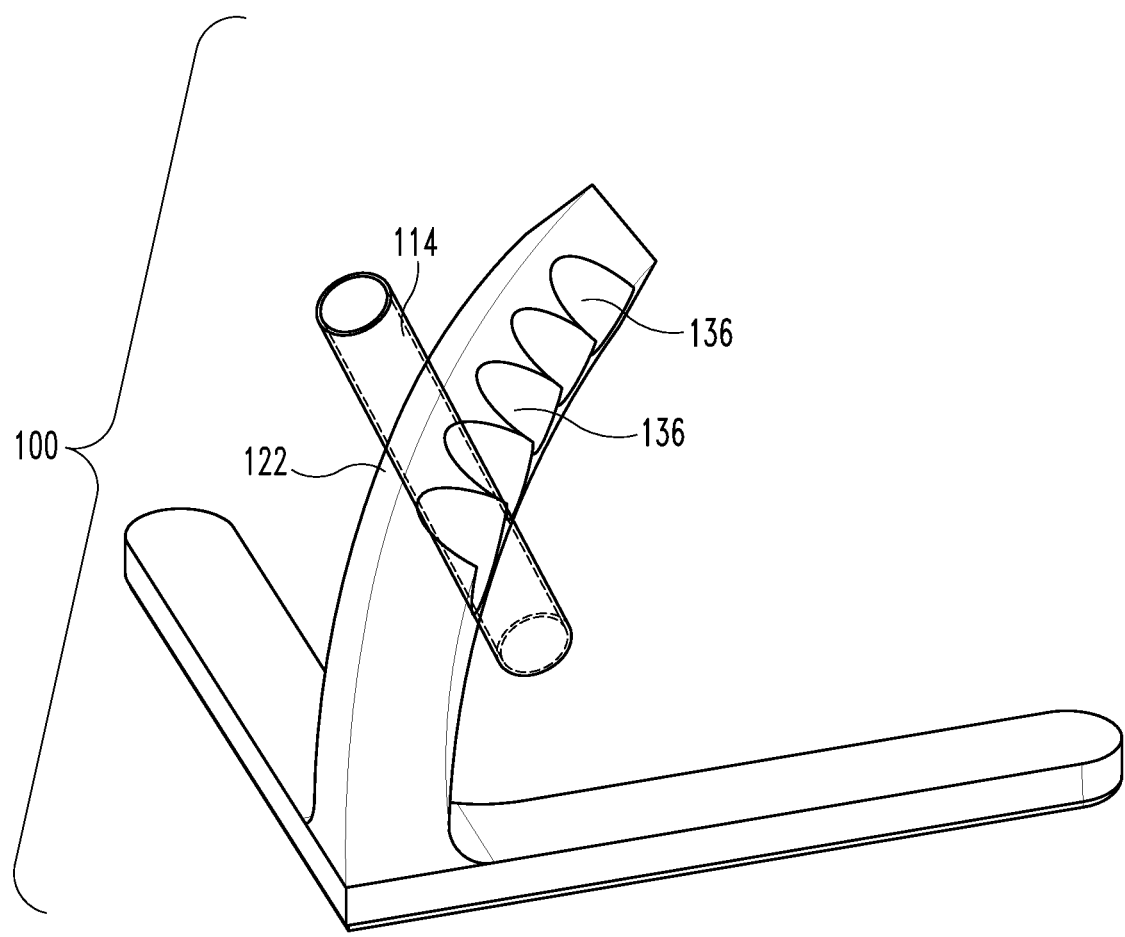
FIG. 3 is a perspective view of another embodiment of a needle stand.

In another embodiment illustrated in FIG. 3, needle stand 100 is illustrated. Needle stand 100 is similar to needle stand 10. Needle stand 100 includes an arching boom 122 similar to boom 22. However, boom 122 defines a plurality of holes 136 along an edge or side of the boom 122. Needle stand 100 also includes a tube 114 similar to tube 14. In this embodiment, the plurality of holes 136 is configured to form a snap-fit connection when tube 114 is inserted therein. That is, in this embodiment the diameter of holes 136 is about the same as or slightly less than that of tube 114, and the openings in boom 122 allowing entry to holes 136 are smaller than the diameter of tube 114. Further, in this embodiment the snap-fit design of the plurality of holes 136 retains the tube 114. Accordingly, a key or other additional locking mechanism is not needed.

While the invention has been illustrated and described in detail in the drawings and foregoing description, the same is to be considered as illustrative and not restrictive in character, it being understood that only the preferred embodiment has been shown and described and that all changes, equivalents, and modifications that come within the spirit of the inventions defined by following claims are desired to be protected. All publications, patents, and patent applications cited in this specification are herein incorporated by reference as if each individual publication, patent, or patent application were specifically and individually indicated to be incorporated by reference and set forth in its entirety herein. It is to be understood that features described with respect to one embodiment or part may be used with other embodiments or parts.

The invention claimed is:

1. An apparatus to support a biopsy needle, the apparatus comprising:
    a tube sized to retain the biopsy needle; and
    a stand for securely holding said tube, said stand including a base having a plurality of legs, an arching boom attached to and supported by the base, the boom having a length that has a convex curvature relative to the base, the boom defining a plurality of holes along its length, wherein each of the plurality of holes is sized to receive the tube and each of the plurality of holes is configured to adjust from an open position wherein the tube is moveable relative to the boom and a closed position wherein the tube is restrained from movement in one of the plurality of holes.

2. The apparatus of claim 1, wherein the plurality of legs includes two legs, and the two legs are separated from each other by an angle of about 90°.

3. The apparatus of claim 1, wherein the plurality of legs includes three legs that are in one plane.

4. The apparatus of claim 1, wherein each of the plurality of legs has a top surface opposite a bottom surface, the bottom surface having an adhesive to attach the base to a medical patient.

5. The apparatus of claim 1, wherein the length of the arching boom is about 7.0 cm.

6. The apparatus of claim 1, wherein the arching boom includes a first side opposite a second side and the plurality of holes are positioned between the first and second sides, the arching boom has a proximal boom portion opposite a distal boom portion, the distal boom portion defining a slot between the first and second sides that communicates with at least one of the holes and a pair of key holes that extend through the first and second sides; and
   a key configured to move in the pair of key holes and squeeze the first and second sides together to secure the tube in one of the plurality of holes.

7. The apparatus of claim 6, wherein the first and second sides are tapered from the distal boom portion to the proximal boom portion.

8. The apparatus of claim 6, wherein the key is a thumbscrew, and the pair of key holes are threaded so as to threadedly engage the thumbscrew.

9. The apparatus of claim 1, wherein each of the holes overlaps with at least one other of the holes.

10. An apparatus to support a biopsy needle, the apparatus comprising:
   a tube sized to retain the biopsy needle;
   a base configured to attach to a patient, wherein the base defines a plane; and
   an arching boom attached to the base, the arching boom having a length that is a convex curvature relative to the base, the arching boom defines a plurality of holes along the length, each of the plurality of holes is sized to receive and retain the tube at an elevation that is adjustable relative to the boom and each of the plurality of holes defines an axis, wherein the plane and each of the axes form a unique point of entry angle for the biopsy needle in a medical patient.

11. The apparatus of claim 10, wherein the base includes a plurality of legs.

12. The apparatus of claim 10, wherein each of the plurality of holes is spaced at an interval along the arching boom that corresponds to about 10° increment in the point of entry.

13. The apparatus of claim 10, wherein the tube and the biopsy needle form an interference fit connection.

14. The apparatus of claim 10, wherein the arching boom includes a first side opposite a second side and the plurality of holes is positioned between the first and second sides, the arching boom has a proximal boom portion opposite a distal boom portion, the distal boom portion defining a slot between the first and second sides communicating with at least one of the holes and a pair of key holes that extend through the first and second sides; and
   a key configured to move in the pair of key holes and squeeze the first and second sides together to secure the tube in one of the plurality of holes.

15. The apparatus of claim 10, wherein the arching boom includes a centerline along the length and the plurality of holes are positioned along the centerline.

16. The apparatus of claim 10, wherein the arching boom includes a side edge along the length and the plurality of holes are positioned along the side edge.

17. An apparatus to support a biopsy needle, the apparatus comprising:
   a base configured to attach to a patient, wherein the base defines a plane; and
   an arching boom attached to the base, the arching boom having a length that is a convex curvature relative to the base, the arching boom defines a plurality of holes along the length, each of the plurality of holes is adjustably sized to receive and retain the biopsy needle at an elevation that is adjustable relative to the boom, and each of the plurality of holes defines an axis wherein the plane and each of the axes form a unique point of entry angle for the biopsy needle in a medical patient.

18. The apparatus of claim 17, wherein the base includes a first arm rotationally offset from a second arm, the first arm and the second arm being generally in the same plane.

19. The apparatus of claim 18, wherein the first arm and the second arm are flexible to conform to a body surface of the medical patient.

20. The apparatus of claim 17, further comprising:
   a tube sized to retain the biopsy needle; and
   wherein each of the plurality of holes is sized to receive and retain either the tube or the biopsy needle at an elevation that is adjustable relative to the boom.

* * * * *